United States Patent [19]

Gabele et al.

[11] Patent Number: 5,508,006
[45] Date of Patent: Apr. 16, 1996

[54] STERILIZATION CONTAINER FOR SURGICAL INSTRUMENTS OR THE LIKE

[75] Inventors: Lorenz Gabele, Sauldorf; Uwe Kulow, Tuttlingen; Wolfgang Schwanke, Weilheim; Wolfgang Taschner, Tuttlingen, all of France

[73] Assignee: Aesculap AG, Tuttlingen, Germany

[21] Appl. No.: 411,751

[22] PCT Filed: Feb. 6, 1993

[86] PCT No.: PCT/EP93/00283
§ 371 Date: Mar. 30, 1995
§ 102(e) Date: Mar. 30, 1995

[87] PCT Pub. No.: WO94/08632
PCT Pub. Date: Apr. 28, 1994

[30] Foreign Application Priority Data

Oct. 16, 1992 [DE] Germany .............................. 9213983 U
Dec. 2, 1992 [DE] Germany .............................. 9216378 U

[51] Int. Cl.⁶ ..................................................... A61L 2/26
[52] U.S. Cl. ........................ 422/119; 422/297; 422/300; 206/459.5; 206/807
[58] Field of Search ..................... 422/119, 297, 422/300, 310; 436/1; 206/438, 439, 63.5, 459.5, 807; 116/200, 311, 312, 294

[56] References Cited

U.S. PATENT DOCUMENTS 4,562,047 12/1985 Sestak et al. ........................ 422/119
4,820,499 4/1989 Taschner .............................. 422/119
4,915,913 4/1990 Williams et al. .................... 422/119
5,328,661 7/1994 Taschner .............................. 422/119
5,382,528 1/1995 Scoville .............................. 422/300

FOREIGN PATENT DOCUMENTS 3316141 11/1984 Germany .
WO92/06899 4/1992 WIPO .

Primary Examiner—Robert J. Warden
Assistant Examiner—Theresa T. Snider
Attorney, Agent, or Firm—Barry R. Lipsitz; Ralph F. Hoppin

[57] ABSTRACT

In order to facilitate the detection of any unauthorized opening of a sterilization container for surgical instruments or the like having a lower section, a cover sealingly placeable thereon, a locking member securing the cover in position on the lower section and pivotable between a closed position and an open position, and a card-like securing element which can be secured in position on the container and moves into the path of travel of the locking member near to the closed position of the locking member, it is suggested that the part of the securing element moving into the path of travel of the locking member be elastically bendable out of the plane of the securing element and move into the path of travel of the locking member only to such a depth that it slides back behind the locking member when the locking member is pivoted into the open position and during closing of the locking member is taken along with it and is covered by the locking member in the closed position thereof.

21 Claims, 3 Drawing Sheets

STERILIZATION CONTAINER FOR SURGICAL INSTRUMENTS OR THE LIKE

BACKGROUND OF THE INVENTION

The invention relates to a sterilization container for surgical instruments or the like, with a lower section, a cover sealingly placeable thereon, a locking member securing the cover in position on the lower section and being pivotable between a closed position and an open position, and a card-like securing element which can be secured in position on the container and moves into the path of travel of the locking member near to the closed position of the locking member.

Such a sterilization container is known from German patent No 35 41 309. The card-like securing element is normally used at the same time as a data carrier, on which essential data concerning the contents of the container and the type of treatment are indicated. The known design has the advantage that any unauthorized opening of the locking member following a sterilization procedure damages the securing element and so it is possible to subsequently recognize every unauthorized opening of the container due to this damage. In known securing elements, this damage is in the form of a punch mark which can easily be seen on the securing element once removed but is difficult to recognize when the securing element is inserted and held on the container since it is concealed by the punching element held on the locking member.

SUMMARY OF THE INVENTION

The object of the invention is to develop a sterilization container of the type described at the outset further such that it can be detected immediately from the inserted securing element whether or not any unauthorized opening of the container has taken place.

This object is accomplished in accordance with the invention, in a sterilization container of the type described at the outset, in that the part of the securing element moving into the path of travel of the locking member can be bent elastically out of the plane of the securing element and moves into the path of travel of the locking member only to such a depth that it slides back behind the locking member when the locking member is pivoted into the open position and during closing of the locking member is taken along with it and is covered by the locking member in the closed position thereof. Therefore, a part of the securing element which is located in front of the locking member after closure of the container is bent forwards by the locking member when this is opened and then slides behind the locking member so that it is covered by this locking member when the locking member is closed again. This means that it can be seen at a first glance whether any opening of the locking member has taken place. This is ruled out only when the part moving into the path of travel of the locking member is located in front of the locking member and not covered or concealed by it.

It is favorable for the part moving into the path of travel of the locking member to be a tongue protruding laterally from the card-like securing element.

In a preferred embodiment, it is possible for a holder for the card-like securing element to be arranged next to the locking member, the securing element being insertable or slidable into the holder following the closure of the locking member such that the part moving into the path of travel of the locking member is positioned directly in front of the locking member. The holder is therefore secured in position, for example, directly next to the locking member on the side wall of the lower section so that it is located essentially in the same plane as the closed locking member.

It is particularly advantageous for the part moving into the path of travel of the locking member to be bent forwardly out of the plane of the card-like securing element after its insertion into the holder due to it abutting on the locking member. This means that this bent part of the securing element is particularly conspicuous and visible so that it is recognizable at a first glance that the locking member has not so far been opened.

In this respect, it is possible for the locking member to have a deflecting surface, along which the part of the card-like securing element moving into the path of travel of the locking member is deflected to in front of the locking member during insertion into the holder so that the user of the container, during insertion, need not pay any particular attention to a part of the securing element being placed in front of the locking member since this takes place automatically during insertion due to this deflecting surface.

The holder can have an insertion slot for the securing element on its side facing away from the locking member, this insertion slot preferably being laterally offset in relation to the plane, in which the securing element can be positioned in the holder. This lateral offset means that the card-like securing element can be pushed into the holder only when deformed and bent and after its insertion into the holder can no longer be pushed out of the holder in the reverse direction since the elastic securing element cannot pass into the laterally offset slot when displaced in the reverse direction. This is a safety measure to prevent the securing element being pushed out of the path of travel of the locking member in order to open the locking member in an unauthorized and uncontrolled manner. After the insertion of the securing element, this remains in the holder until completion of the procedure and can be withdrawn from the holder only after the locking member has been opened.

In a particularly preferred embodiment, the part of the card-like securing element moving into the path of travel of the locking member is connected to the rest of the securing element by means of a predetermined breaking point and by means of a stronger, flexible connection and the predetermined breaking point is designed and positioned such that it breaks when the locking member takes along the part of the securing element lying in front of it during pivoting into the open position whereas the stronger connection remains. This special construction means, on the one hand, that the securing element is permanently altered due to damage to the predetermined breaking point as soon as the locking member is pivoted once into the open position while, on the other hand, the part of the securing element moving into the path of travel of the locking member remains connected to this securing element and so when the locking member is closed again this part is taken along to behind the locking member, despite the damage to the predetermined breaking point, and is covered by it.

For this purpose, the part moving into the path of travel of the locking member can be connected with the rest of the securing element via two connecting webs of different widths; in another embodiment it is also possible for an opening to be arranged in the securing element next to the part moving into the path of travel of the locking member, this opening forming a broad and a narrow connecting web between the part moving into the path of travel and the rest of the securing element.

In this respect, it is particularly advantageous for the locking member to bear a lateral extension which engages between the connecting webs during pivoting of the locking member into the open position and during further pivoting thus tears the narrow connecting web.

In another embodiment, it is possible for the locking member to bear a marking member which penetrates and thus damages the securing element during pivoting of the locking member out of the closed position into the open position. Such damage to the securing element, which is known per se from DE-PS 35 41 309, can likewise serve to mark the securing element as soon as the locking member is pivoted once into the open position. Nevertheless, the part moving into the path of travel remains connected to the securing element in this solution, as well, so that it is possible to recognize immediately on the container, even when the securing element is inserted, whether the locking member has been opened or not.

In a further, preferred embodiment, it is possible for a holding-down element to be arranged next to the part of the securing element positioned in front of the locking member, this holding-down element being located in front of the securing element and securing this in position in a direction towards the sterilization container. In such a construction, the securing element is held in one section near to the wall of the sterilization container while another part is located in front of the locking member. When the securing element is damaged in this region, for example by an improper, prior opening, this means that the securing element protrudes forwards at an angle in the region in front of the locking member.

It is particularly advantageous for the holding-down element to secure the securing element in a position, in which the securing element is biased in an outward direction away from the sterilization container between the region covered by the holding-down element and the region located in front of the locking member. An undamaged securing element will not be essentially deformed by this biasing since the securing element is secured in position by the holder essentially parallel to the plane of insertion of the securing element. When, however, a section of the securing element is ripped or punched out so that this part is now held only on one side on the securing element, this biasing then leads automatically to this region protruding outwardly out of the plane of the securing element, and this is immediately recognizable for the operator.

The holding-down element can be part of the locking member.

It is particularly advantageous for a gap extending parallel to the direction of insertion of the securing element to be arranged in the locking member, the holding-down element which covers the securing element being arranged on one side of this gap and a part of the locking member located under the securing element being arranged on the other side of the gap, this part of the locking member sliding past the securing element when the locking member is opened and covering the securing element once the locking member has been closed again. In this embodiment, the securing element slides automatically into the gap when inserted into the holder, a part of the securing element thereby sliding under the locking member so that the locking member, in this case, takes over the function of a holding-down element while the other part slides onto the locking member. When the locking member is opened, the tearing of the predetermined breaking point is made easier, in particular, in a design damaging the securing element.

In another embodiment, the holding-down element can, however, also be part of the holder for the securing element.

The following description of a preferred embodiment of the invention serves to explain the invention in greater detail in conjunction with the drawings.

DETAILED DESCRIPTION OF THE INVENTION

Figure 1:
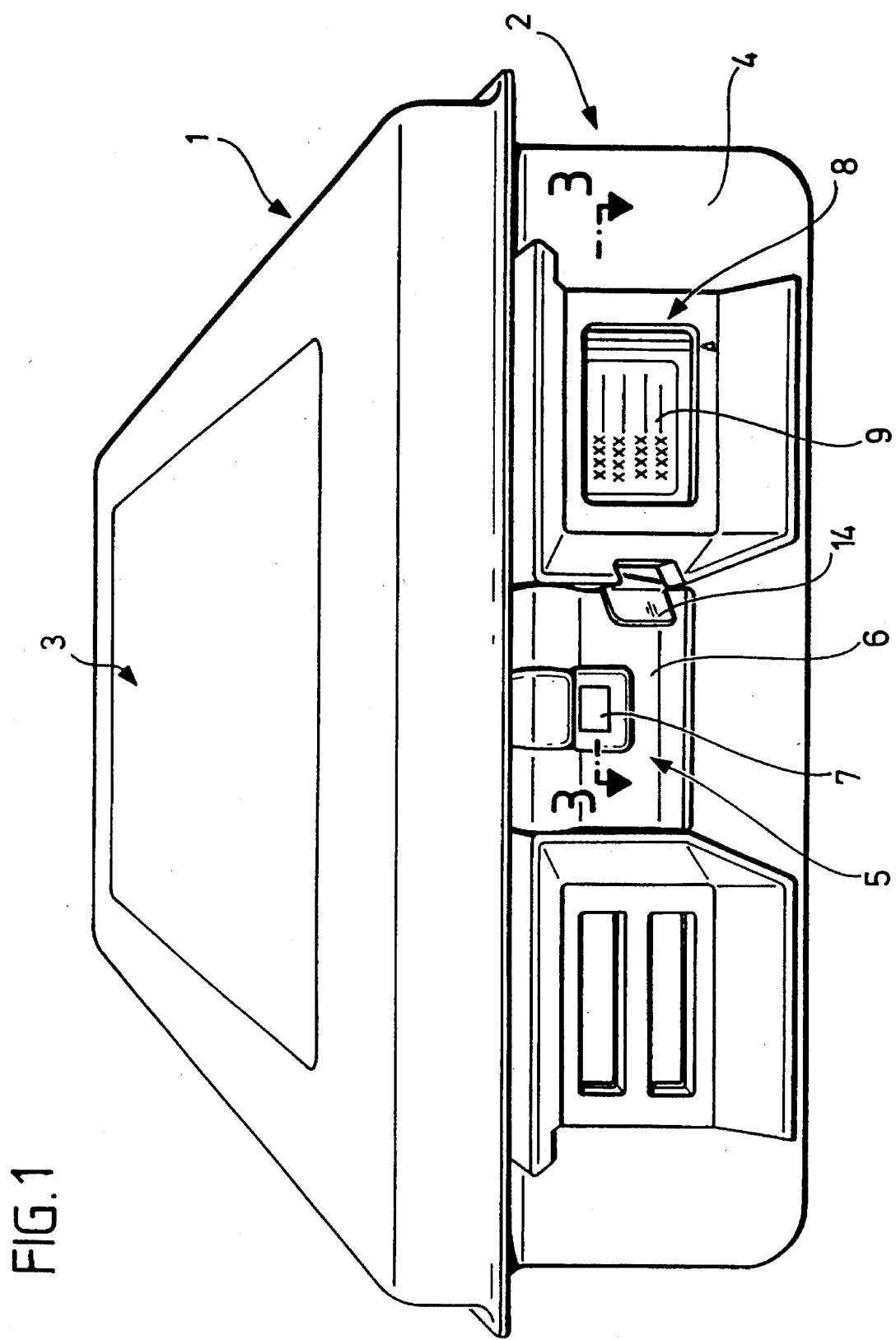
FIG. 1 is a perspective plan view onto a sterilization container with a locking member closure means and a card-like securing element.

The sterilization container 1 illustrated in FIG. 1 comprises a tub-shaped lower section 2 as well as a cover 3 which can be placed sealingly on this lower section 2. A closure means 5 is arranged on a front side wall and, where applicable, also on a side wall lying opposite thereto and not illustrated in the drawings, the closure means fixing the cover 3 in position on the lower section 2. This closure means comprises in the illustrated embodiment a locking member 6 which is mounted on the cover 3 so as to pivot about a horizontal axis and in a lowered, closed position, in which it is arranged essentially parallel to the side wall 4, engages around a closure element 7 on the side wall 4 whereas it releases this closure element 7 when it is swung out to the front about the horizontal axis. The nature of this closure means is not of importance for the present invention; for this reason, this closure means is also not explained in greater detail. It is, of course, possible to use the most varied of closure mechanisms in this case; it is also possible for the locking member to be mounted on the side wall instead of on the cover. For the present invention it is merely essential for the closure means to have a locking member pivotable between a closed position and an open position.

An insertion holder 8 for a card-like securing element 9 is arranged on the side wall 4 next to the locking member 6. The securing element can be arranged in this insertion holder 8 so as to extend parallel to the side wall 4 in a plane which is essentially coplanar to the outer side of the locking member 6 in the closed position; if required, this plane could also be set slightly back in relation to the outer side of the locking member 6 in the direction towards the container.

Figure 2:
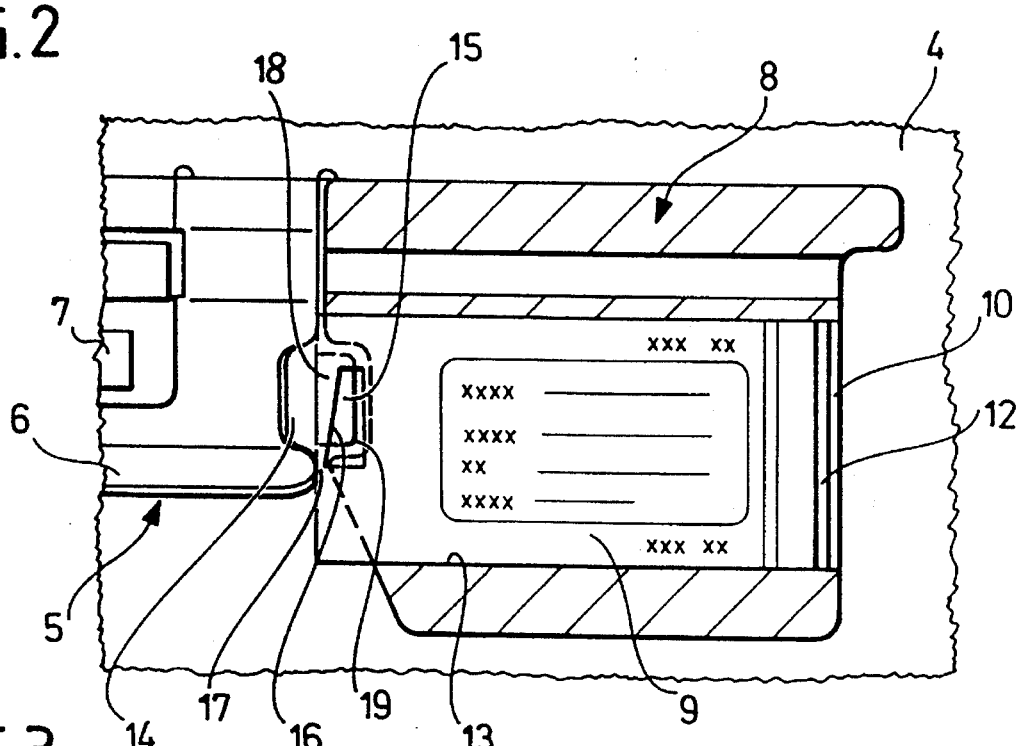
FIG. 2 is an enlarged partial view of the holder for the securing element in a section parallel to the side wall of the container.
Figure 3:
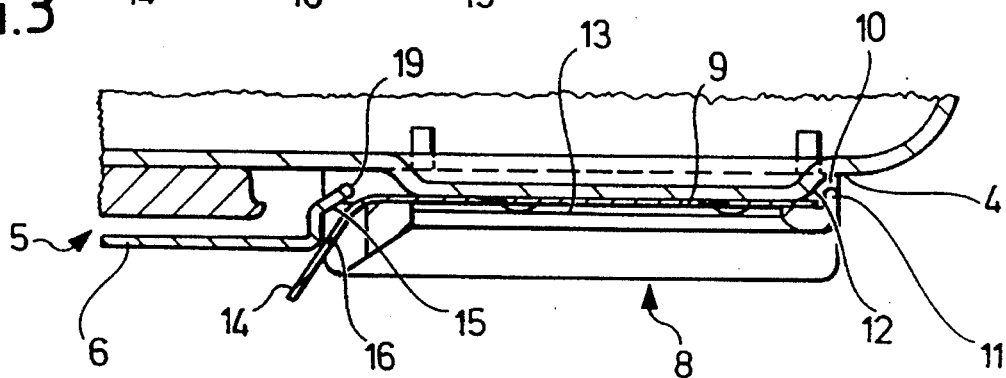
FIG. 3 is a sectional view along line 3—3 with a securing element prior to the opening of the locking member.
Figure 4:
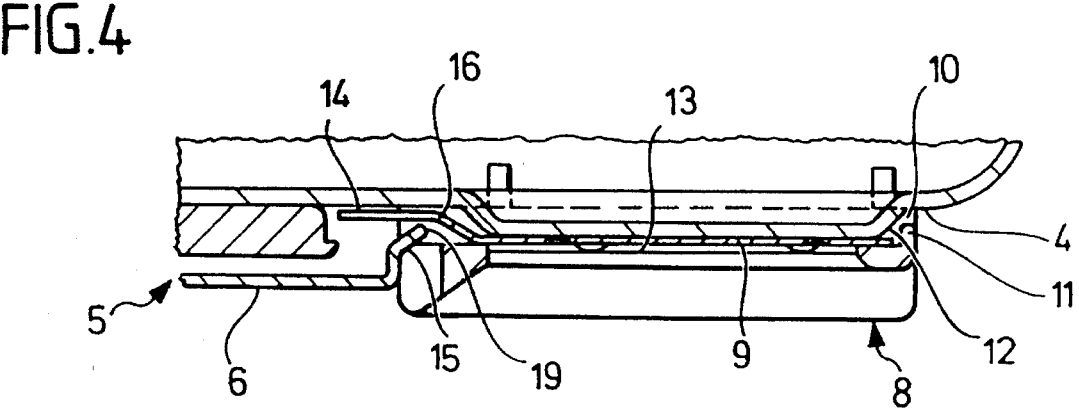
FIG. 4 is a view similar to FIG. 3 with the securing element after the opening and reclosing of the locking member.

In FIG. 2 the insertion holder 8 has on the side facing away from the locking member 6 an insertion slot 10 which is set slightly back in the direction towards the side wall 4 in relation to the plane, in which the card-like securing element 9 is held in the insertion holder 8 (FIGS. 3 and 4). This is brought about in that the insertion holder 8 has an edge 11 on the side facing away from the locking member 6 which is bent at right angles and directed towards the side wall 4. Directly adjacent the insertion slot 10, the side wall 4 forms a deflecting surface 12 which deflects the card-like securing element 9, after insertion into the insertion slot 10, into the plane, in which the securing element 9 is held in the insertion holder 8.

A slot 13 arranged in the plane of the insertion holder 8 is also arranged in the insertion holder 8 on the side opposite the insertion slot 10 and therefore directly adjacent the locking member 6. A part 14 of the card-like securing element 9 protrudes out of the insertion holder 8 through this slot and moves into the path of travel of the locking member 6. This protruding part 14 is, in the illustrated embodiment, designed as a tongue protruding laterally from the card-like securing element 9. When the locking member 6 is closed, this tongue is pushed in front of the locking member by a lateral deflecting surface 15 on the locking member 6, whereby the tongue is bent at an angle outwards in the manner shown in FIG. 3.

The card-like securing element 9 has an opening 16 immediately adjacent the part 14 designed as a tongue and this opening forms two connecting webs between the part 14 and the remaining area of the securing element 9, namely a narrow connecting web 17 and a broad connecting web 18.

The deflecting surface 15 on the locking member 6 is also designed in the shape of a tongue and reaches with its outer edge 19 as far as into the region of the opening 16 of the securing element 9 inserted into the insertion holder 8 (FIG. 2) so that the edge 19 enters the opening 16 when the locking member is opened.

When using the sterilization container, the container is first of all closed by pivoting the locking member 6 into the closed position when the cover 3 is in place. Once the container has been closed, a card-like securing element, on which data concerning the contents of the container and the necessary treatment steps can be entered, is pushed into the insertion holder 8 through the lateral insertion slot 10. The part 14 designed as a tongue thereby slides along the deflecting surface 15 of the locking member and moves in front of the locking member in the manner shown in FIG. 3, whereby the tongue protrudes at an angle outwards. It is easily recognizable in this position and indicates that the locking member has remained closed.

If the locking member is opened, the edge 19 engages in the opening 16 and thereby tears the narrow connecting web 17 whereas the broad connecting web 18 remains intact. When the locking member 6 is pivoted further into an open position, the part 14 which is now connected with the securing element 9 only via the broad connecting web 18 slides along the side edge of the locking member and swivels into the path of travel of the locking member again behind the locking member so that when the locking member is closed again it takes the part 14 along and covers it, as shown in FIG. 4. Due to the fact that the tongue is no longer visible in front of the locking member in the manner apparent from FIG. 3 but is covered by the locking member in the manner apparent from FIG. 4, the user can easily recognize that the locking member has been opened unintentionally.

If the securing element is pulled out of the insertion holder 8 through the slot 13 after the locking member has been opened, it is immediately recognizable due to the torn, narrow connecting web 17 that the locking member has been unintentionally opened during the course of treatment. In this way, complete certainty is obtained concerning the treatment history of the container contents, in particular when, according to a preferred embodiment, a sterilization indicator field is also arranged on the securing element 9, i.e. a field which is subject to a change in color during sterilization. Proper treatment can first be recognized on the container due to the fact that the change in color has taken place and that the tongue is located in front of the locking member. Proper treatment can be recognized on the securing element 9 itself by the change in color and by the fact that both the narrow connecting web 17 and the broad connecting web 18 are intact.

It is also not possible to open the locking member without damaging the securing element since the securing element can be removed from the insertion holder only when the locking member is opened, namely only through the slot 13, since it is not possible to push it out in the opposite direction due to the lateral offset of the insertion slot 10. This ensures altogether the greatest possible security.

Figure 5:
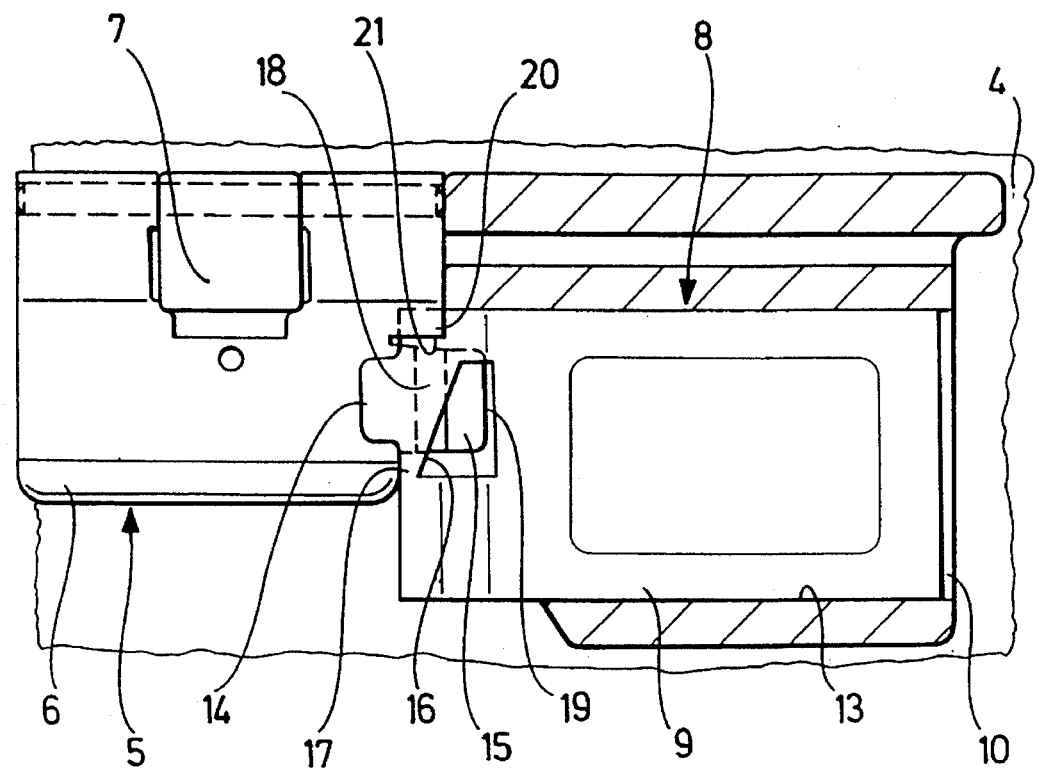
FIG. 5 is a view similar to FIG. 2 in another preferred embodiment of a locking member closure means and FIG. 6 is a view similar to FIG. 3 in the embodiment of FIG. 5.
Figure 6:
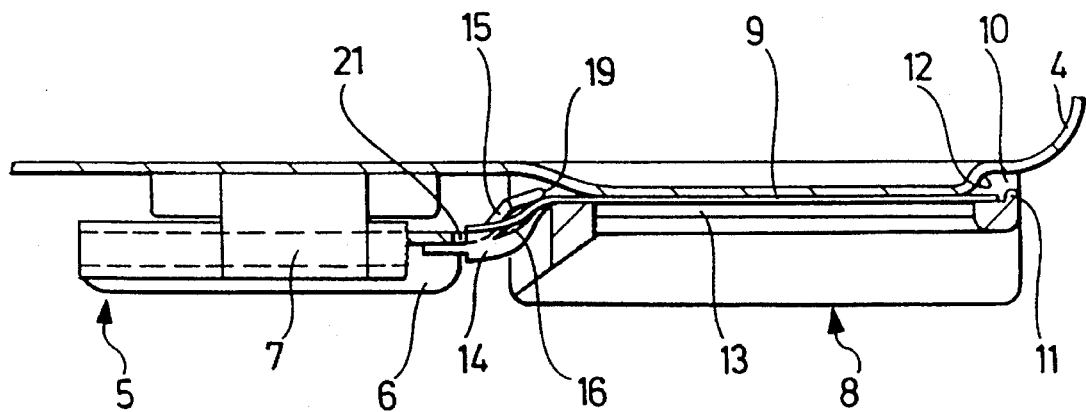

In the embodiment illustrated in FIGS. 5 and 6, only minor amendments have been made in comparison with the embodiment of FIGS. 1 to 4; corresponding parts therefore have the same reference numerals.

In the embodiment of FIGS. 5 and 6, a surface acting as a holding-down element 20 follows on from the deflecting surface 15 engaging beneath the securing element 9. This surface is separated from the deflecting surface 15 by a gap 21 extending in the holder 8 from the outer edge of the locking member 6 inwards parallel to the direction of insertion of the securing element 9. When the securing element 9 is inserted into the insertion holder 8, the deflecting surface 15 deflects the securing element 9 to a position which is in front of the locking member in the region of the deflecting surface 15, but behind the locking member in the region of the holding-down element 20, the securing element 9 thereby entering the gap 21. In this respect, the arrangement is selected such that the securing element 9, after its insertion, is biased towards the outside in the region of the gap 21.

As long as the securing element is undamaged in the manner shown in FIG. 5, this biasing leads at the most to a slight deformation of the securing element and the part of the securing element connected with the rest of the securing element via the webs 17 and 18 also lies in front of the locking member and essentially parallel to it, as shown in FIG. 5.

When, however, the narrow web 17 of the securing element 9 is damaged for any reason, the biasing in the region of the gap 21 results in the part, which is now connected to the securing element 9 only via the broad web 18, protruding outwardly, i.e. it is immediately recognizable that the securing element is damaged. This also provides a way of ensuring that a damaged securing element is not used, i.e. this results in an additional check as to whether securing elements used in the holder are in perfect condition.

We claim:

1. A sterilization container comprising:

a lower section;

a cover sealingly placeable on said lower section;

a locking member securing the cover in position on the lower section and mounted on one of said cover and lower section for pivotable movement between a closed position and an open position;

a card-like securing element positionable on one of said cover and lower section of the container and having a portion movable into a path of travel of said locking member;

said movable portion being elastically bendable out of the plane of the rest of said securing element for placement into the path of travel of the locking member only to such an extent that it slides behind the locking member when the locking member is pivoted into an open position, said locking member upon closing causing said movable portion of the securing element to move along said path of travel such that said movable portion is covered by said locking member when said locking member reaches said closed position.

2. A sterilization container as defined in claim 1 wherein said movable portion comprise a tongue protruding laterally from said card-like securing element.

3. A sterilization container as defined in claim 1 further comprising a holder for said card-like securing element, said holder being arranged next to said locking member for receiving said securing element when said locking member is closed, with said movable portion positioned directly in front of said locking member.

4. A sterilization container as defined in claim 3 wherein said movable portion is bent forwardly out of said plane by abutment with said locking member when the card-like securing element is inserted into said holder.

5. A sterilization container as defined in claim 3 wherein said locking member includes a deflecting surface for deflecting said movable portion of said card-like securing element in front of the locking member during insertion of said securing element into said holder.

6. A sterilization container as defined in claim 3 wherein said holder comprises an insertion slot for said securing element, said insertion slot being provided at a side of said holder opposite said locking member.

7. A sterilization container as defined in claim 6 wherein said insertion slot is laterally offset in relation to the plane in which the securing element is held in said holder.

8. A sterilization container as defined in claim 3 further comprising means operatively associated with said locking member for holding said securing element down in a position towards said sterilization container, said holding down means being arranged in front of a portion of said securing element next to said movable portion thereof.

9. A sterilization container as defined in claim 8 wherein said holding down means are part of said locking member.

10. A sterilization container as defined in claim 9 further comprising:

a gap arranged in said locking member and extending parallel to the direction of insertion of said securing element;

said holding down means covering said securing element being arranged on one side of said gap; and a part of said locking member being arranged on the other side of said gap and under the securing element;

said part of said locking member being designed and positioned to slide past the securing element when the locking member is opened and to cover the securing element once the locking member has been closed again.

11. A sterilization container as defined in claim 8 wherein said holding down means are part of the holder for the securing element.

12. A sterilization container as defined in claim 1 wherein:

said movable portion is connected to the rest of said securing element via a first connection having a predetermined breaking point, and a second stronger, flexible connection;

said predetermined breaking point of said first connection is designed and positioned such that said first connection breaks when the locking member moves said movable portion when pivoted into said open position; and said second connection is designed and positioned such that it remains intact when said first connection breaks.

13. A sterilization container as defined in claim 12 further comprising a holder for said card-like securing element, said holder being arranged next to said locking member for receiving said securing element when said locking member is closed, with said movable portion positioned directly in front of said locking member.

14. A sterilization container as defined in claim 13 wherein said movable portion is bent forwardly out of said plane by abutment with said locking member when the card-like securing element is inserted into said holder.

15. A sterilization container as defined in claim 12 wherein said first connection comprises a connecting web having a first width;

said second connection comprises a connecting web having a second width; and said first width is different from said second width.

16. A sterilization container as defined in claim 15 wherein said locking member bears a lateral extension engaging between the connecting webs for tearing the narrower one of said webs when the locking member is pivoted into said open position.

17. A sterilization container as defined in claim 12 wherein an opening is arranged in said securing element next to said movable portion, said opening defining said first connection and said second connection between said movable portion and the rest of the securing element; wherein said first connection comprises a connecting web having a first width, said second connection comprises a connecting web having a second width; and said first width is narrower than said second width.

18. A sterilization container as defined in claim 17 wherein said locking member bears a lateral extension engaging between the connecting webs for tearing said narrow web when the locking member is pivoted into said open position.

19. A sterilization container as defined in claim 12 further comprising means operatively associated with said locking member for holding said securing element down in a position towards said sterilization container, said holding down means being arranged in front of a portion-of said securing element next to said movable portion thereof.

20. A sterilization container as defined in claim 1 wherein said locking member bears a marking member for penetrating and damaging said securing element during pivoting of the locking member out of the closed position into the open position.

21. A sterilization container as defined in claim 1 further comprising:

means operatively associated with said locking member for holding said securing element down in a position towards said sterilization container, said holding down means being arranged in front of a portion of said securing element next to said movable portion thereof;

wherein said holding down means secure the securing element in a position such that a region of the securing element which is located between a region covered by said holding down means and a region located in front of said locking member is biased in an outward direction away from the sterilization container.

* * * * *